United States Patent [19]

Collins et al.

[11] 4,020,090
[45] Apr. 26, 1977

[54] ORGANOTIN COMPOUNDS

[75] Inventors: John Desmond Collins, Albrighton; Harold Coates, Wombourn; Iftikhar Hussain Siddiqui, Birmingham, all of England

[73] Assignee: Albright & Wilson Limited, West Midlands, England

[22] Filed: Nov. 19, 1974

[21] Appl. No.: 525,119

Related U.S. Application Data

[63] Continuation-in-part of Ser. No. 308,018, Nov. 20, 1972, abandoned.

[30] Foreign Application Priority Data

Nov. 19, 1971 United Kingdom ............ 53892/71

[52] U.S. Cl. .................... 260/429.7; 260/45.75 K; 260/346.1 M
[51] Int. Cl.² ........................................ C07F 7/22
[58] Field of Search ............. 260/429.7, 346.1 M, 260/45.75 K, 45.75 T

[56] References Cited

UNITED STATES PATENTS

| | | | |
|---|---|---|---|
| 2,680,107 | 6/1954 | Leistner et al. | 260/429.7 X |
| 2,910,452 | 10/1959 | Crauland | 260/429.7 X |
| 2,998,441 | 8/1961 | Mack et al. | 260/429.7 |
| 3,078,290 | 2/1963 | Hechenbleikner et al. | 260/429.7 |
| 3,126,400 | 3/1964 | Cramer et al. | 260/429.7 |
| 3,209,017 | 9/1965 | Hechenbleikner et al. | 260/429.7 |
| 3,217,004 | 11/1965 | Hechenbleikner et al. | 260/429.7 |
| 3,450,668 | 6/1969 | Kawakami et al. | 260/45.75 |
| 3,534,121 | 10/1970 | Eggensperger et al. | 260/429.7 X |
| 3,544,510 | 12/1970 | Stapfer | 260/429.7 X |
| 3,654,222 | 4/1972 | Stapfer et al. | 260/45.75 T |
| 3,890,276 | 6/1975 | Stapfer | 260/45.75 S |

FOREIGN PATENTS OR APPLICATIONS 1,309,140   3/1973   United Kingdom

*Primary Examiner*—Helen M. S. Sneed

[57] ABSTRACT

Novel organotin compounds exhibit the general formula

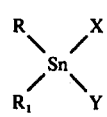

where R and $R_1$ are individually selected from the group consisting of $C_1$ and $C_{12}$ alkyl groups, cycloalkyl radicals and phenyl radicals; X is a group of the formula

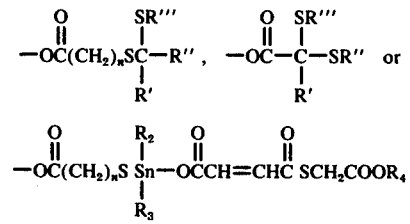

wherein R' is a hydrogen, $C_1$ to $C_{20}$ alkyl, cycloalkyl, or phenyl group;

R'' is a $C_1$ to $C_{20}$ alkyl, phenyl, hydroxyphenyl, or methoxyphenyl group or the radical $CH_2COOR_5$, where $R_5$ is an alkyl radical of 1 to 8 carbon atoms;

R''' is $R_6$ or is $(CH_2)_n COOR_6$ where $R_6$ is an alkyl radical of from 1 to 20 carbon atoms, a cycloalkyl or a phenyl radical, m is an integer from 3 to 7 and n is an integer from 1 to 4;

$R_2$ and $R_3$ are selected from the same group as R;

$R_4$ is selected from the same group as R';

Y is selected from the same group of groups as X or exhibits a formula selected from the group consisting of $S(CH_2)_nCOOR_7$, $OOCCH{=}CHCOOR_7$ and $OOCCH{=}CHCOSCH_2COOR_7$, with the proviso that Y is

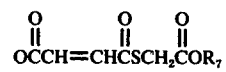

when X is

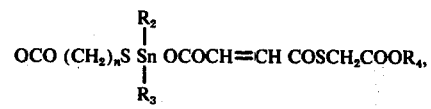

where $R_7$ is an alkyl group of from 1 to 20 carbon atoms, a cycloalkyl or phenyl group or a radical of the formula

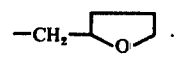

These compounds are of use as stabilizers for the homopolymer or copolymers of vinyl chloride.

35 Claims, No Drawings

ORGANOTIN COMPOUNDS

This application is a continuation-in-part of application Ser. No. 308,018, filed Nov. 20, 1972 and now abandoned. U.S. Pat. No. 3,928,284 issued on Ser. No. 463,452 which was filed on Apr. 24, 1974 as a division of said Ser. No. 308,018. U.S. Pat. No. 3,928,284 contains claims directed to stabilized resin compositions.

The present invention relates to organotin compounds and to their use as stabilizers for polymeric materials, in particular halogenated resins such as polymers and copolymers of vinyl and vinylidene chloride.

The use of organotin compounds containing sulfur as stabilizers for halogenated resins has for many years been recognized as being highly effective. However, the compounds employed have normally been those having a comparatively high tin content and so, in view of the high cost of tin, are expensive relative to other available stabilizers. Thus, despite their high efficiency these compounds are still not as widely used as other, less effective, materials.

The compounds of the present invention are sulfur-containing organotin compounds which have a lower tin content than most conventional sulfur-containing organotin compounds and so are potentially cheaper. The stabilizing ability of some of them may match that of some of the conventional materials and so may be able to achieve the same degree of stabilization for lower cost.

Accordingly, the present invention provides a new chemical compound having the general formula

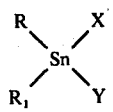

where R and $R_1$ are individually selected from the group consisting of $C_1$ to $C_{12}$ alkyl groups, cycloalkyl and phenyl groups;

X is a group of the formula

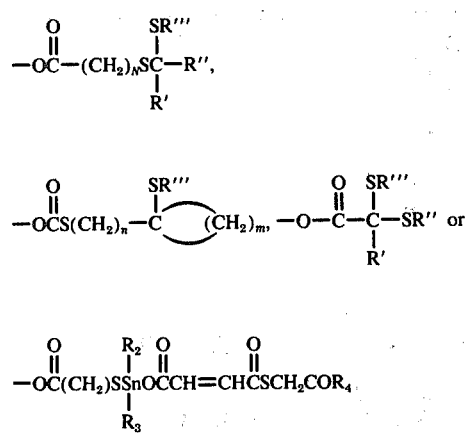

wherein R' is a hydrogen, $C_1$ to $C_{20}$ alkyl, cycloalkyl, or phenyl group;

R'' is a $C_1$ to $C_{20}$ alkyl, phenyl, hydroxyphenyl or methoxyphenyl group or the radical $CH_2 COOR_5$ where $R_5$ is a short chain alkyl group of 1 to 8 carbon atoms;

R''' is $R_6$ or is $(CH_2)_n COOR_6$ where $R_6$ is an alkyl group of from 1 to 20 carbon atoms, a cycloalkyl or a phenyl group, $m$ is an integer from 3 to 7 and $n$ is an integer from 1 to 4;

$R_2$ and $R_3$ are selected from the same group as R;

$R_4$ is selected from the same group as R';

Y is selected from the same group of groups as X or exhibits a formula selected from the group consisting of $-S(CH_2)_n COOR_7, -OOCCH=CH\ COOR_7$ or $-OOCCH=CH\ COSCH_2COOR_7$, with the proviso that Y is $-OCCH=CHCSCH_2COR_7$ when X is

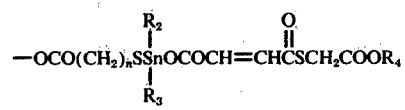

where $R_7$ is an alkyl group of from 1 to 20 carbon atoms, a cycloalkyl or phenyl group or a group of the formula

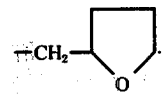

From another aspect the present invention provides a process for preparing compounds of the formula

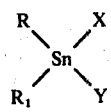

which comprises reacting a diorganotin oxide of the formula

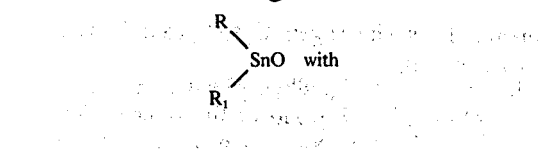

1. a first mixture of
   a. an aldehyde or ketone of the formula

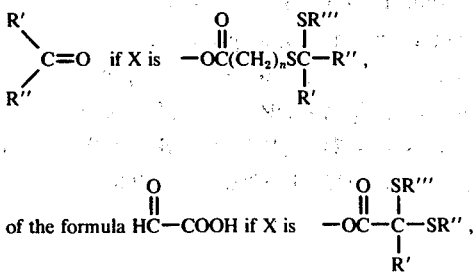

or of the formula $(CH_2)_m C=O$ if

X is $-\overset{O}{\underset{\|}{O}}\overset{}{C}(CH_2)_n\overset{R^3S}{\underset{|}{S}C} (CH_2)_m$, and b. a second mixture of compounds of the formulae R'''SH and HOOC(CH$_2$)$_n$SH if X is

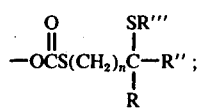

or a mixture of compounds of the formulae R''λ

'SH and R''SH if X is

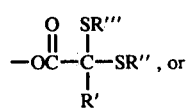

2. the performed reaction product of said first mixture, and optionally a third mixture containing and HOOCCH=CHCOOR$_7$.
HOOCCH=CHCOSCH$_2$COOR$_7$HS(CH$_2$) COOR$_7$ Examples of particular classes of compounds according to the present invention include

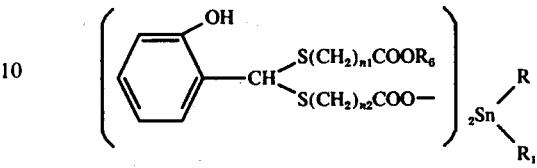

wherein $n1$ and $n2$ are individually selected from integers between 1 and 4, inclusive. Such a compound is derived from

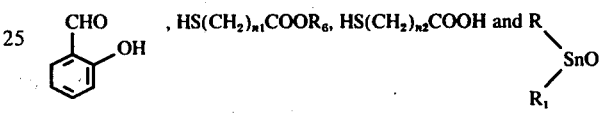

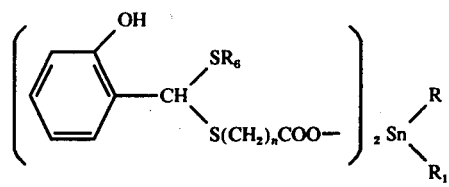

such a compound is obtained from

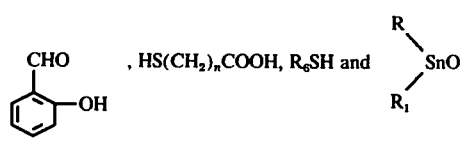

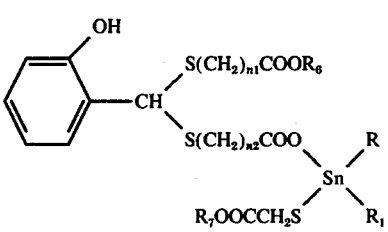

such a compound is obtained from

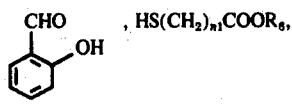, HS(CH$_2$)$_{n1}$COOR$_6$,

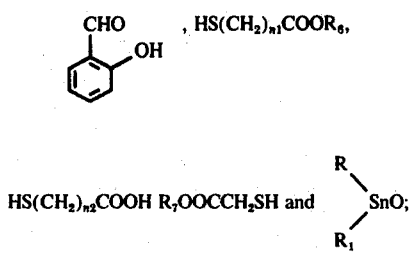

HS(CH$_2$)$_{n2}$COOH R$_7$OOCCH$_2$SH and

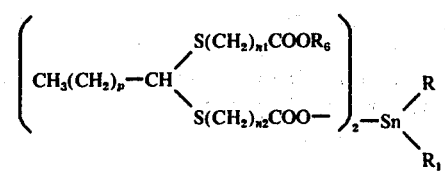

where $p$ is 1 to 12. Such a compound is obtained from CH$_3$(CH$_2$)$_m$CHO, HS(CH$_2$)$_{N1}$COOR$_6$, HS-(CH$_2$)$_{N2}$COOH and

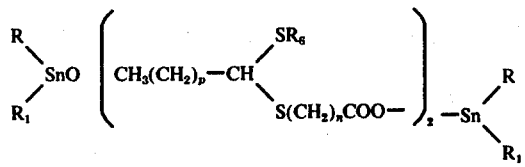

such a compound is obtained from CH$_3$(CH$_2$)$_p$CHO, R$_6$SH,

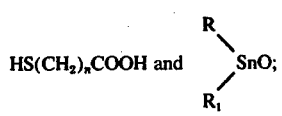HS(CH$_2$)$_n$COOH and

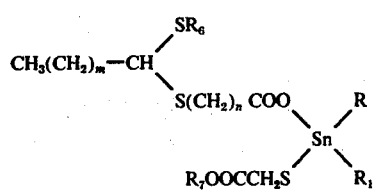

such a compound is obtained from CH$_3$(CH$_2$)$_m$CHO, R$_6$SH, HS(CH$_2$)$_n$COOH, R$_7$OOCCH$_2$SH and

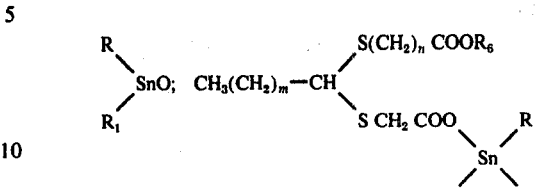

such a compound is obtained from CH$_3$(CH$_2$)$_m$CHO, HS(CH$_2$)$_n$COOR$_6$,

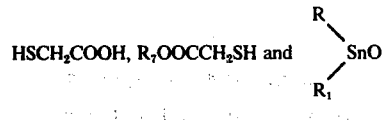

HSCH$_2$COOH, R$_7$OOCCH$_2$SH and

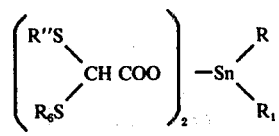

such a compound is obtained from R″SH, R$_6$SH,

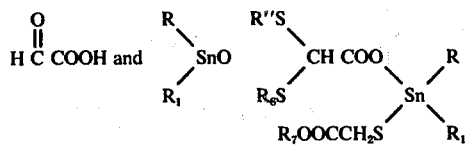

such a compound is obtained from R″SH, R$_6$SH,

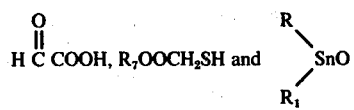

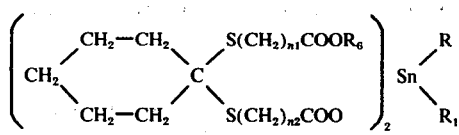

such a compound is obtained from cyclohexane, HS(CH$_2$)$_{n1}$COOR$_6$ HS(CH$_2$)$_{n2}$COOH and

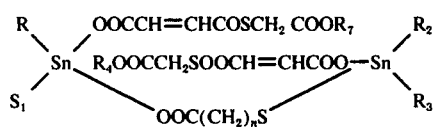

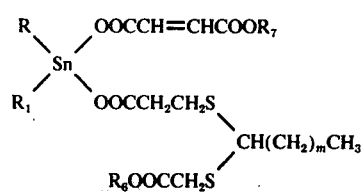

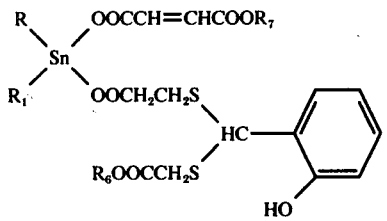

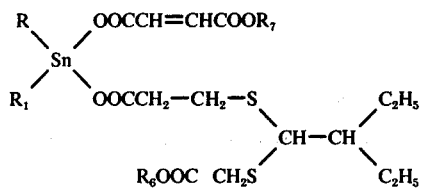

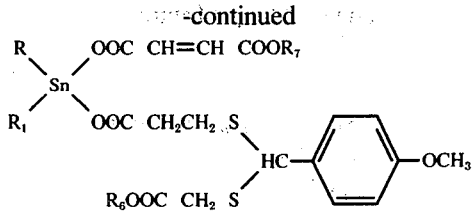

It is normally preferred that all of R, R$_1$, R$_2$ and R$_3$ are the same. Frequently they are alkyl or cycloalkyl groups of from 4 to 8 carbon atoms such as n-butyl, cyclohexyl, n-octyl, iso-octyl or 2-ethylhexyl. R$_6$ is preferably an alkyl group having from 8 to 16 carbon atoms, such as n-octyl, 2-ethylhexyl, lauryl or cetyl. R$_7$ is preferably one of the preferred R$_6$ groups. R' is frequently hydrogen, R" is frequently a straight chain alkyl group of the formula (CH$_2$)$_p$ CH$_3$ where $p$ is 1 to 20, such as an undecanoic group, a shorter branched chain such as secondary amyl, a cycloalkyl group such as a cyclohexyl or substituted cyclohexyl or the group

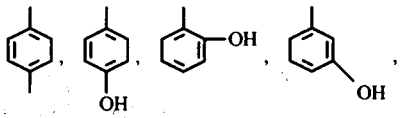

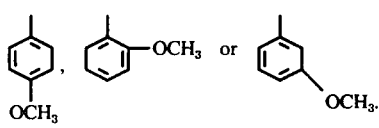

Typical compounds of this invention include:

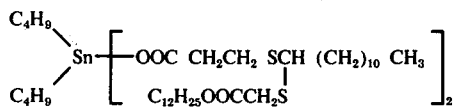

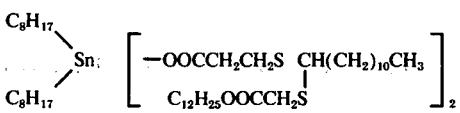

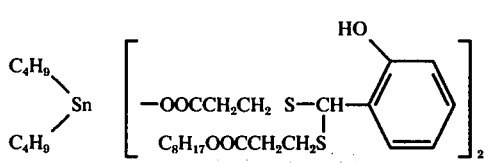

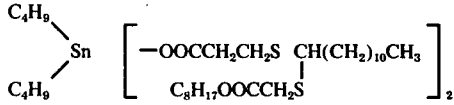

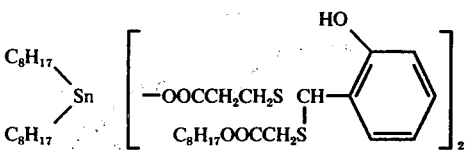

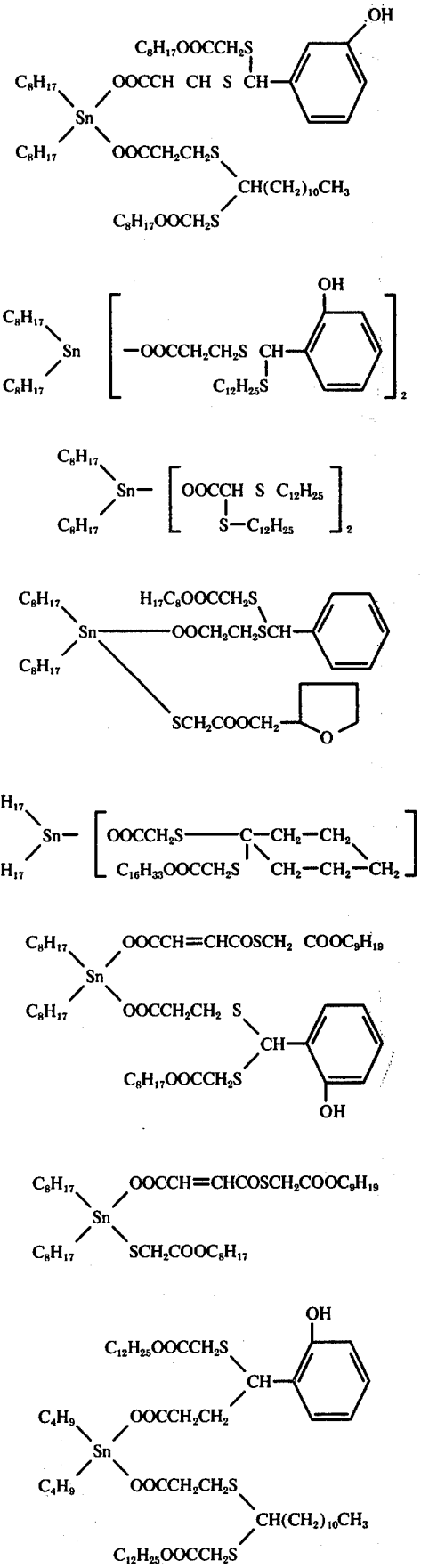
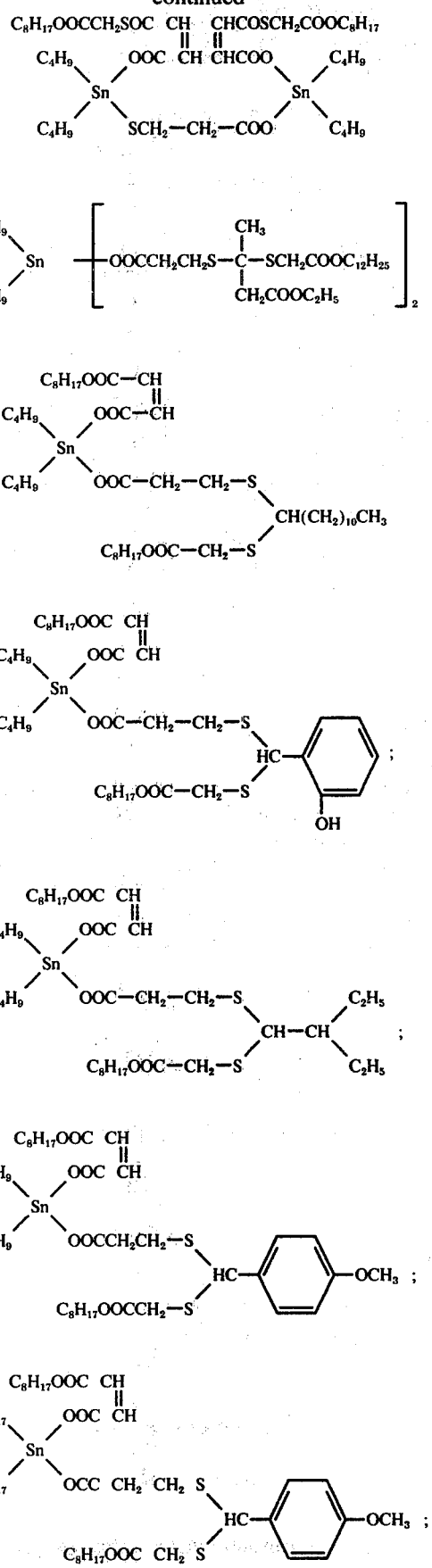

-continued-

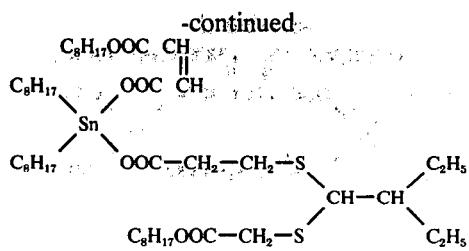

As previously mentioned the compounds of the invention are generally prepared by the reaction of an aldehyde or ketone with a mixture of mercaptan or ester of a thio substituted carboxylic acid such as thioglycolic acid or β-mercapto propionic acid admixed with such an acid. Either during this reaction or subsequently further reaction with a diorganotin oxide is carried out. Either the diorganotin oxide can be caused to react with only one compound formed in this manner or with a mixture of such compounds or it can be caused to react with a mixture of one such compound and a simple thioglycollate or half esterified maleic acid.

As previously mentioned the aldehyde employed may be glyoxylic acid

(HCCOOH), in which case no thio-substituted carboxylic acid will be employed.

Frequently all of the reactants will be mixed together and heated in a suitable solvent, such as benzene, toluene, petrol, xylene, hexane or cyclohexane. Normally it will be desirable to have an acidic catalyst present such as p-toluene sulphonic acid, hydrochloric acid or metal chlorides suitable as Friedel Craft catalysts such as zinc chloride, aluminum trichloride, boron trichloride or stannic chloride.

In the case where the desired product is of the type

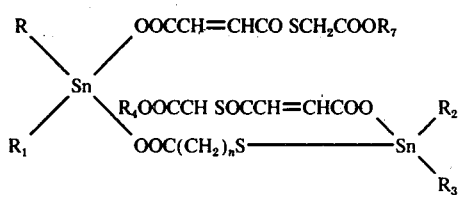

this may be obtained by the reaction under the influence of heat of a thiosemiester of the formula HOOCCH=CHCOSCH$_2$COOR' with a dialkyltin oxide to give an intermediate of the formula

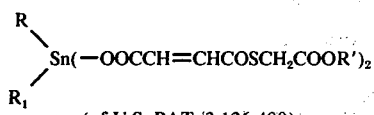

(of U.S. PAT. 3,126,400)

This product is then further reacted with a diorganotin oxide of the formula

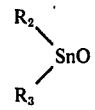

and with a mercaptocarboxylic acid of the formula HS(CH$_2$)$_n$ COOH.

Compounds according to the invention find use as stabilizers for halogen-containing resins which include polymers or copolymers of vinyl chloride or vinylidene chloride, chlorinated vinyl chloride polymers and chlorinated polyethylene. Accordingly, from a further aspect the present invention provides a composition which comprises a halogen-containing resin and as a stabilizer therefor a compound of the formula

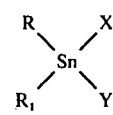

where R, R$_1$, X and Y are as hereinbefore defined.

The organotin compounds will be present in compositions according to the invention in amounts so as to produce the desired stabilizing effect, often this will be from 1 to 5% preferably 2 to 3% by weight based on the total amount of polymeric resin present.

Optionally, but advantageously, compositions according to the invention also contain hindered phenols, that is those having at least one substituent in a position ortho to the hydroxyl group as auxiliary stabilizers. Such phenols which are of use in compositions of the present invention include butylated hydroxyanisol, 2,6-di-tert-butylphenol, methylene bis-(2,4-di-tert-butylphenol), methylene bis-(2,6-di-tert-butylphenol), methylene bis-(2,6-di-tert-butyl-3-methylphenol), 4,4'-butylidene bis-(6-tert-butyl-3-methylphenol), methylene bis-(4-ethyl-6-tert-butylphenol), methylene bis-(4-methyl-2,6-di-tert-butylphenol). Particularly preferred, however, is 2,6-di-tert-butyl-4-methylphenol. Such phenols may be present in an amount of up to 3%, preferably from 0.01 to 0.05% by weight of the resin and will normally be present at about 4–10% by weight, preferably 5–8%, based on the total amount of organotin compounds used.

Esters of phosphorous and thiophosphorous acid may be employed in compositions according to the invention. Such compounds include halo-phosphites such as tris chloropropyl phosphite and polymeric phosphites such as hydrogenated 4,4'-isopropylidene diphenol. Preferred phosphites and thiophosphites, however, are monomers having no substituents in the organo-group and having no more than one sulfur atom. These include triaryl phosphites and trialkyl phosphites. Such compounds include, for example, triphenyl phosphite, trixylylphosphite trinonyl phenyl phosphite and trioctyl phosphite. Diesters of phosphorous acid such as diisopropyl phosphite, dibutyl phosphite and diphenyl phosphite are also of use. Particularly preferred, however, are the mixed alkyl aryl phosphites such as octyl diphenyl phosphite, isodecyl diphenyl phosphite and diisodecyl phenyl phosphite. This particularly pronounced effect may also be obtained by employing a mixture of a triaryl phosphite and an alcohol in conjunction with the organotin compound. A particularly suitable mixture is that of triphenyl phosphite and iso-decanol.

The stabilizer composition is also useful if it is employed in a polymer composition containing an epoxy compound, as may be desired for example in cases where a delay of initial color change is desired. Epoxy compounds which may be employed in such compositions include butyl epoxy stearate, esters of epoxidized oleic acid and compounds of the formula

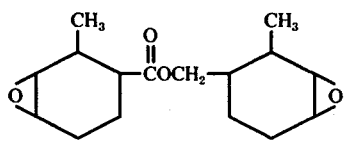

Organotin formulations as described above, optionally including a hindered phenol, an alkylaryl phosphite or aryl phosphite or an epoxide, will often be used as the only stabilizer in a polymeric vinyl chloride or vinylidene chloride composition. However, if desired conventional thermal stabilizers may also be included. These may include, for example, metal soap stabilizers, such as cadmium barium or zinc salts of fatty acids, or lead salts such as lead carbonate or stearate or dibasic lead phosphate or phthalate, or tribasic lead sulphate or conventional organotin stabilizers such as dibutyltin dilaurate or dibutyltin maleate or sulphur-containing compounds such as dibutyltin bis-thioglycollates.

In the practice of the invention the stabilizer formulation may be mixed with the copolymer resin in the conventional manner for example by milling with the resin on heated rolls at about 150° C., although higher temperatures may be used when convenient, or by being mixed with particles of the polymer and then melting and extruding the mixture or by adding the stabilizer to a liquid resin.

Resins which may be used in compositions according to the invention normally contain at least 40% by weight of chlorine. Usually it will be a polymer or copolymer of vinyl chloride or vinylidene chloride but post-halogenated polyvinyl chloride or post-halogenated polyolefins, such as polyethylene, may be employed if desired. Suitable monomers which may form such copolymers with vinyl chloride and vinylidene chloride include for example acrylonitrile, vinyl acetate, methyl methacrylate, diesters of fumaric acid and maleic acid, ethylene, propylene and lauryl vinyl ether. These comonomers may be present in an amount of up to 25% of the total weight of monomers copolymerized.

The organotin stabilizer formulation may be employed in either plasticized resin compositions, for example those plasticized with carboxy ester plasticizers or may be employed in rigid compositions. Such rigid compositions contain little or no plasticizer although for some applications up to about 10% by weight of plasticizer may be present. This is in contrast with plasticized compositions where the amount of plasticizer present is normally greater than 50% by weight of the polymeric material and is often greater than 100% on that basis.

The process of the invention will be illustrated by the following examples:

EXAMPLE 1

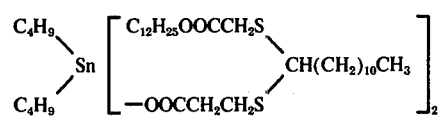

A mixture of β-mercaptopropionic acid (21.2 g., 0.2M), lauryl thioglycollate (52g., 0.2M) and dodecyl aldehyde (36.8g., 0.2M) were heated under reflux in 300 ml. of benzene containing 0.1 gm. of p-toluene sulphonic acid until 3.6 ml. of water had collected. Then 24.9 gm. (0.1M) of dibutyltin oxide was added and refluxing continued until another 1.8 ml. of water had distilled. Benzene was removed from the warm mixture under reduced pressure and finally the product (light yellow liquid) filtered under vacuum.

(Calculated Sn = 9.1%; Found Sn = 9.4%).

EXAMPLE 2

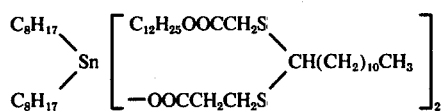

The procedure of Example 1 was followed using the following quantities of reactants:

| | | |
|---|---|---|
| β-mercaptopropionic acid | 10.6g | (0.1M) |
| lauryl thioglycollate | 26.0g | (0.1M) |
| dodecyl aldehyde | 18.4g | (0.1M) |
| dioctyltin oxide | 18.0g | (0.05M) |

The product is a clear yellow liquid.
(Calculated Sn = 8.2%; Found Sn = 8.2%).

EXAMPLE 3

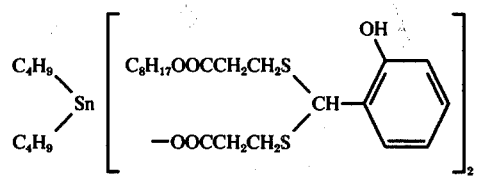

The procedure of Example 1 was followed using the following quantities of reactants (without any catalyst).

| | |
|---|---|
| iso-octyl β-mercaptopropionate | 54.5g (0.25M) |
| β-mercaptopropionic acid | 26.5g (0.25M) |
| Salicyladehyde | 30.6g (0.25M) |
| dibutyltin oxide | 30.1g (0.125M) |

The product is a clear yellow liquid.
(Calculated Sn = 10.9%; Found Sn = 10.7%).

EXAMPLE 4

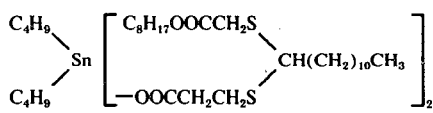

The procedure of Example 1 was followed using the following quantities of reactants (in toluene):

| | |
|---|---|
| dodecylaldehyde | 0.4 M |
| β-mercaptopropionic acid | 0.4 M |
| iso-octyl thioglycollate | 0.4 M |
| dibutyltin oxide | 0.2 M |

The product is a yellow liquid.
(Calculated Sn = 10.0%; Found Sn = 10.1%)

| | |
|---|---|
| S = 10.8%; | S = 11.1% |
| H = 9.4%; | H = 9.6% |
| C = 58.8%; | C = 59.6% |

EXAMPLE 5

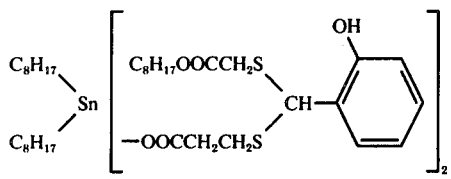

The procedure of Example 1 was followed using the following quantities of reactants (in presence of very small quantity of zinc chloride (0.1g) instead of p-toluene sulphonic acid):

| | |
|---|---|
| Salicylaldehyde | 30.6g (0.25M) |
| iso-octyl thioglycollate | 51.0g (0.25M) |
| β-mercaptopropionic acid | 26.5g (0.25M) |
| dioctyltin oxide | 45.1g (0.125M) |

The product is a clear oily liquid.
(Calculated Sn = 10.1%; Found Sn = 10.0%).

EXAMPLE 6

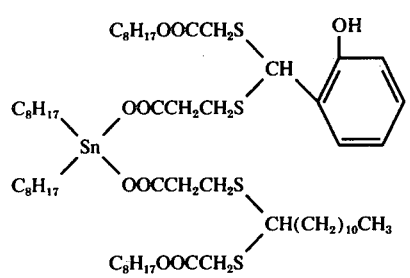

A mixture of 1-mercaptopropionic acid 1-mercapto isooctyl glycollate 2-n-decyl ethane

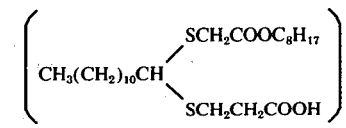

(0.05 M, prepared as in Example 4 step 1), 2-hydroxy benzal (mono mercaptopropionic acid mono mercapto isooctyl glycollate)

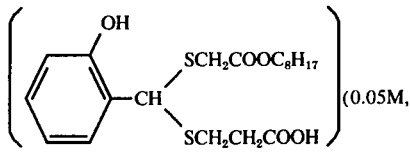

prepared as in Example 5 step 1) and dioctyltin oxide (0.05M) were heated under reflux in benzene until calculated amount of water had collected. The benzene was removed and finally the product filtered under vacuum.

The product is a clear yellow liquid.
(Calculated Sn = 9.6%; Found Sn = 9.8%)

EXAMPLE 7

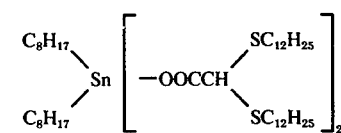

The product of Example 1 was followed using the following quantities of reactants (using conc. hydrochloric acid and water mixture, 1 ml (ratio 1:3 respectively) instead of p-toluene sulphonic acid):

| | | |
|---|---|---|
| salicylaldehyde | 24.4g | (0.2M) |
| β-mercaptopropionic acid | 26.5g | (0.2M) |
| lauryl mercaptan | 40.1g | (0.2M) |
| dioctyltin oxide | 36.1g | (0.1M) |

The product is a yellow liquid.
(Calculated Sn = 10.17%; Found Sn = 10.56%).

EXAMPLE 8

A mixture of di(lauryl sulphide) acetic acid (46g., 0.1M) and dioctyltin oxide (18.0g., 0.05M) were heated in benzene (300 ml) till the calculated amount of water had collected. The hot mixture was filtered rapidly under reduced pressure, which on cooling at room temperature gave a waxy solid product. The waxy solid was filtered under reduced pressure and then dried on a filter paper to complete the evaporation of benzene.

(Calculated Sn = 9.4%; Found Sn = 10.3%).

EXAMPLE 9

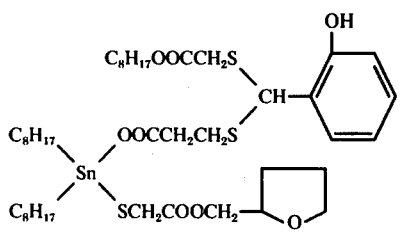

A mixture of

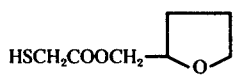

(0.1M), 2-hydroxy benzal (mono-mercaptopropionic acid mono-mercapto isooctyl glycollate) (0.1M) and dioctyltin oxide (0.1M) were heated under reflux in benzene (250 ml). The yellow product was obtained by the same method as in Example 6.

(Calculated Sn = 12.7%; Found Sn = 11.3%)

EXAMPLE 10

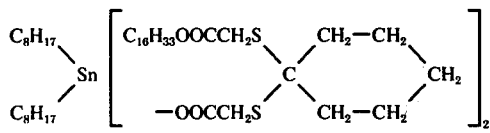

Cyclohexyl 1, 1-bis (mercapto acetic acid) (52.8g., 0.2M) and cetyl alcohol (48.4g., 0.2M) were reacted in toluene in presence of p-toluene sulphonic acid to give monocetyl derivative of cyclohexyl 1,1-bis(mercapto-acetic acid).

36.07g (0.1M) of dioctyltin oxide was added into the above mixture, and the mixture further refluxed until the calculated amount of water had collected as above.

The product is a yellow liquid.

(Calculated Sn = 9.0%; Found Sn = 8.9%).

EXAMPLE 11

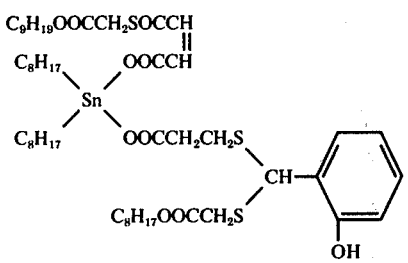

The thiosemiester (C$_9$H$_{19}$OOCCH$_2$SOCCH = CHCOOH) was prepared by reacting nonylthioglycollate (1M) and maleic anhydride (1.1M) in toluene (400 ml) under reflux for one hour. The reaction mixture was cooled, washed in a separating funnel three times with water and then dried over sodium sulphate.

Toluene was removed from the product by distillation under reduced pressure and finally it was filtered under vacuum.

Thiosemiester (0.1M), 2-hydroxy benzal (mono mercaptopropionic acid mono mercapto isooctyl thioglycollate (0.1M) and dioctyltin oxide (0.1M) were reacted as in Example 6.

The product is a yellow liquid.

(Calculated Sn = 11.0%; Found Sn = 11.3%).

EXAMPLE 12

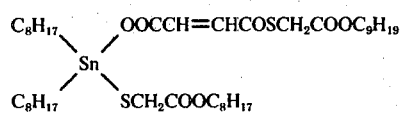

The thiosemiester (3.6g., 0.1M), isooctylthioglycollate (20.4g., 0.1M) and dioctyltin oxide (36.07g., 0.1M) were reacted in benzene as in Example 6.

The product is a yellow liquid.

(Calculated Sn = 13.6%; Found Sn = 13.1%).

EXAMPLE 13

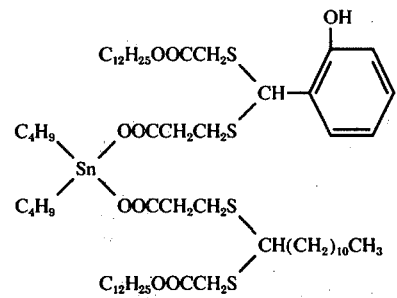

The procedure of Example 6 was followed using the following quantities of reactants (in presence of one drop of conc. hydrochloric acid).

| (a) | 1-mercaptopropionic acid 1-mercaptolauryl glycollate 2-n-decyl ethane | 0.15M |
| (b) | 2-hydroxy benzal (monomercaptopropionic acid mono-mercapto lauryl glycollate) | 0.15M |
| (c) | dibutyltin oxide | 0.15M |

This product is a light yellow liquid.
(Calculated Sn = %.6%; Found Sn = 10.2%).

EXAMPLE 14

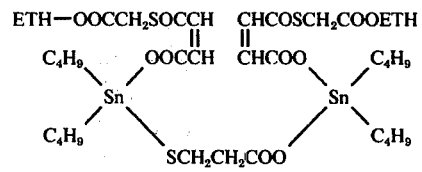

(where ETH represent 2-ethyl hexyl)

A mixture of thiosemiester (HOOCCH=CHCOSCH$_2$COOETH) (60.4g., 0.2M, prepared as in Example 11), dibutyltin oxide (24.9g., 0.1M) and toluene (250 ml) was refluxed in a Dean Stark apparatus until 1.8 ml of water had collected to give Bu$_2$Sn(—OOCCH=CH-COSCH$_2$COOETH)$_2$. Dibutyltin oxide (24.9g., 0.1M)

was further added and the mixture again heated until a clear liquid containing

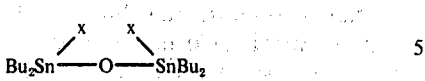

(where x= —OOCCH=CHCOSCH COOETH) was obtained. 10.6g (0.1M) of β-mercaptopropionic acid was added and the resulting mixture again refluxed until 1.8 ml of water were removed. The toluene was then distilled off under reduced pressure and the product recovered as a light yellow liquid after filtering under vacuum.

(Calculated Sn = 20.2%; Found Sn = 20.05%).

EXAMPLE 15

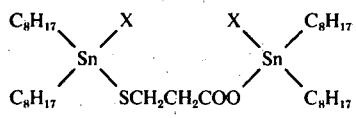

(where X = —OOCCH=CHCOSCH$_2$COO 2-ethyl hexyl)

The procedure of Example 14 was followed using the following quantities of reactants:

| (a) | ETH—OOCCH$_2$SOCCH=CHCOOH | 60.4g | (0.2M) |
| (b) | dioctyltin oxide | 36.07g | (0.1M) |
| (c) | dioctyltin oxide | 36.07g | (0.1M) |
| (d) | β-mercaptopropionic acid | 10.6g | (0.1M) |

The product is a yellow liquid.
(Calculated Sn = 17.0%; Found Sn = 17.9%).

EXAMPLE 16

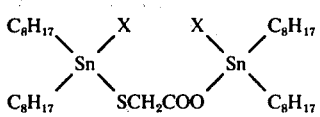

(where X = —OOCCH=CHCOSCH$_2$COO isooctyl).

The procedure of Example 14 was followed and the product is a yellow liquid.

EXAMPLE 17

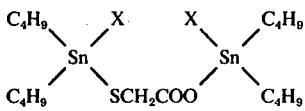

(where X = —OOCCH=CHCOSCH$_2$COO isooctyl)

The procedure of Example 14 was followed and the product is a yellow liquid.

EXAMPLE 18

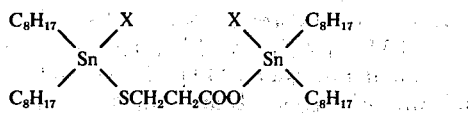

(where X = —OOCCH=CHCOSCH$_2$COOC$_9$H$_{19}$)

The procedure of Example 14 was followed and the product is a yellow liquid.

EXAMPLE 19

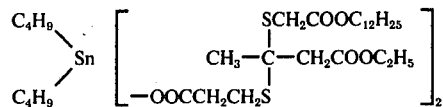

The procedure of Example 1 was followed using the following quantities of reactants:

| (a) | Ethyl aceto-acetate | 13 | g. | (0.1M) |
| (b) | β-mercaptopropionic acid | 10.6 | g. | (0.1M) |
| (c) | Lauryl thioglycollate | 26.0 | g. | (0.1M) |
| (d) | Benzene | 150 | ml | |
| (e) | HCl (50% Conc. HCl + 50% H$_2$O) | 0.5 | ml | |
| (f) | Dibutyltin oxide | 12.5 | g. | (0.05M) |

The product is a light yellow liquid.

EXAMPLE 20

The stabilizers of the present invention can be used with halogen containing vinyl and vinylidene resins in which the halogen is attached directly to the carbon atoms of the polymer chain. Preferably, the resin is a vinyl halide resin, especially a vinyl chloride resin.

The stabilizers of the present invention can be incorporated with resin by admixing in an appropriate mill or mixer or by any of the other well known methods which provide for uniform distribution throughout the resin compositions. Thus mixing can be accomplished by milling on rolls at 100°–155° C. In addition to the novel stabilizers these can also be incorporated with resin conventional additives such as plasticizers, pigments, filters, dyes and ultraviolet absorbing agents.

If a plasticizer is employed, it is used in conventional amount e.g. 30 to 150 parts per 100 parts of resin. Typical plasticizers are di-2-ethyl hexyl phthalate, dibutyl sebacate, di-isooctyl phthalate, and tricresyl phosphate.

The tin containing stabilizers are normally used in an amount of 0.01 to 10% by weight of the resin. More preferably 0.2 to 5% of the tin compound is used by weight of the resin.

The following example illustrates the stabilizing effect of the additives of the present invention.

A series of rigid (non-plasticized) formulation was prepared having following composition:

| (a) | Corvic D55/9 | 100 Parts |
| (b) | Plastilube 30 (marked x if being added) | 0.5 or 1 Part |
| (c) | Stabilizer | 2 Parts (See Table I or 1 Part (See Table II) |

The stabilizer was added in the proportion as above and was fused (after thorough mixing) on a two-roller mill at 154° C (309° F) for 5 minutes. Samples were cut from the sheet and heated in an oven at 190° C (374° F).

Samples were withdrawn at 5 minute intervals and the discoloration (yellow) were noted by comparison with the Gardner scale.

TABLE I

| No. | STABILIZER | Color after .... min at 190° C | | | | |
|---|---|---|---|---|---|---|
| | | 0 | 5 | 10 | 15 | 20 |
| (1)* | Mellite 31. ++ | 0 | 0 | 2 | 4 | 5 |
| (2) | Example 10 | 0 | 0 | 1 | 2 | 3 |
| (3) | Example 19 | 0 | 0 | 1 | 3 | |
| (4) | Example 3 | 0 | 0 | 1 | 2 | 4 |
| (5) | Example 12 | 0 | 1 | 4 | 4 | 6 |
| (6) | Example 1 | 0 | 0 | 1 | 3 | 5 |
| (7) | Example 5 | 0 | 0 | 1 | 1 | 2 |
| (8) | Example 6 | 2 | 3 | 4 | 4 | |
| (9) | Example 8 | 1 | 2 | 4 | 8 | |
| (10) | $Bu_2SnX_2$ ++ | 1 | 1 | 3 | 5 | |
| (11) | $OC_2SnX_2$xx | 1 | 1 | 3 | 5 | |
| (12) | Example 4 | 0 | 0 | 2 | 4 | |

+ Mellite 31 = Dibutyltin bis-isooctyl thioglycollate.
xx Sn stabilizer used = 1.96 parts instead of 2 parts
++ Compounds tested for comparative purposes only.
$X_2$—OCCCH=CHCOSCH$_2$COO iso Octyl

TABLE II

| No. | Stabilizer | Color after .... min at 190° C | | | | |
|---|---|---|---|---|---|---|
| | | 0 | 5 | 10 | 15 | 20 |
| (1)* | Mellite 31 | 1 | 1 | 3 | 5 | 6 |
| (2) | Example 14 | 0 | 0 | 0 | 1 | 3 |
| (3) | Example 17 | 0 | 0 | 0 | 1 | 3 |
| (4) | Example 15 | 0 | 0 | 0 | 1 | 8 |

*Mellite 31 = Dibutyltin bis-isooctyl thioglycollate.

EXAMPLE 21

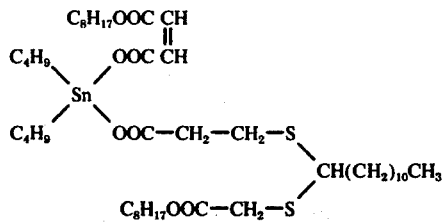

0.1 mole of HOOC CH=CH COOC$_8$H$_{17}$ (prepared from maleic anhydride and isooctyl alcohol), 0.1 mole of

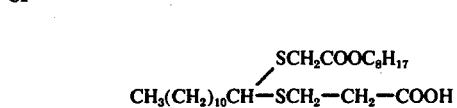

(prepared from dodecylaldehyde, iso-ocyle thioglycollate and β-mercaptoprionic acid) and 0.1 mole of dibutyltic oxide were refluxed in tuluene until the calculated amount of water had collected in Dean Stark apparatus.

The product is a light yellow liquid.

| Analysis | Found | | Calculated |
|---|---|---|---|
| Sn = | 12.7% | Sn = | 12.7% |
| S = | 7.5% | S = | 6.8% |
| C = | 58.1% | C = | 57.7% |
| H = | 8.79% | H = | 9.0% |

Its structure was also confirmed by I.R. and N.M.R. analysis.

EXAMPLE 22

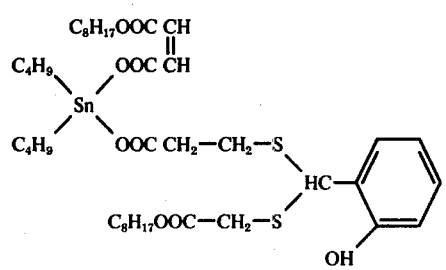

It was prepared by the same method as in Example 21, using the following starting materials:

| (A) | HOOC CH=CH COO C$_8$H$_{17}$ | 0.1M |
|---|---|---|
| (B) | $(C_4H_9)_2$ SnO | 0.1M |
| (C) | [structure shown] | 0.1M |

(C was prepared from salicylaldehyde, isooctyl thioglycollate and β-mercaptopropionic acid).
The product is a light yellow liquid.

| Analysis | Found | | Calculated |
|---|---|---|---|
| Sn = | 14.1% | Sn = | 13.6% |
| S = | 8.4% | S = | 7.3% |

Its structure was also confirmed by I.R. and N.M.R. analysis.

EXAMPLE 23

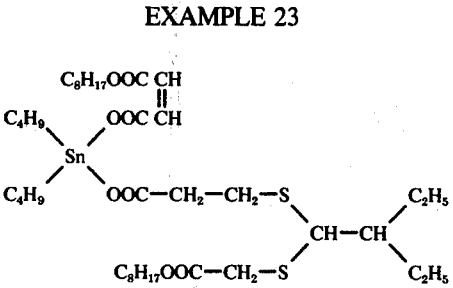

It was prepared by the same as in Example 21 using the following starting materials:

| (A) | HOOC CH=COOC$_8$H$_{17}$ | 0.1M |
|---|---|---|
| (B) | $(C_4H_9)_2$SnO | 0.1M |
| (C) | [structure shown] | |

(C was prepared from isooctyl thioglycollate, β-mercaptoprionic acid and 2-ethylbutyraldehyde).
The product is a light yellow liquid.

Analysis

| | Found | | Calculated |
|---|---|---|---|
| Sn = | 13.4% | Sn = | 13.9% |
| S = | 7.5% | S = | 7.5% |
| C = | 56.63% | C = | 55.1% |
| H = | 7.98% | H = | 8.4% |

The structure was also confirmed by I.R. and N.M.R. analysis.

EXAMPLE 24

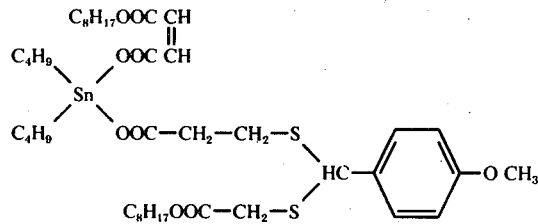

It was prepared by the same method as in Example 21, using the following starting materials:

| | | |
|---|---|---|
| (A) | HOOC CH=CH COOC$_8$H$_{17}$ | 0.1M |
| (B) | (C$_4$H$_9$)$_2$ SnO | 0.1M |
| (C) | CH$_3$O—C$_6$H$_4$—CH(S—CH$_2$—COOC$_8$H$_{17}$)(S—CH$_2$—CH$_2$—COOH) | 0.1M |

(C was prepared from isooctyl thioglycollate, $\beta$-mercaptopropionic acid and anisaldehyde).

The product is a yellow liquid.

Analysis

| | Found | | Calculated |
|---|---|---|---|
| Sn = | 12.7% | Sn = | 13.4% |
| S = | 7.1% | S = | 7.2% |
| C = | 56.27% | C = | 56.6% |
| H = | 7.29% | H = | 7.6% |

EXAMPLE 25

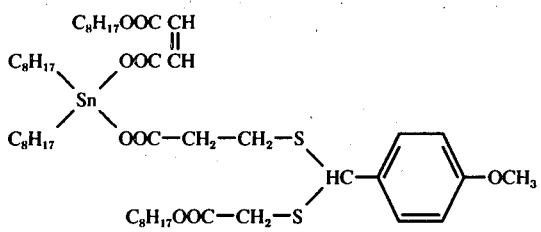

It was prepared by the same method as in Example 24 (using dioctyltin oxide 0.1M., instead of dibutyltin oxide).

The product is a yellow liquid.

Analysis

| | Found | | Calculated |
|---|---|---|---|
| Sn = | 11.5% | Sn = | 11.8% |
| S = | 6.5% | S = | 6.4% |

Its structure was also confirmed by I.R. and N.M.R. analysis.

EXAMPLE 26

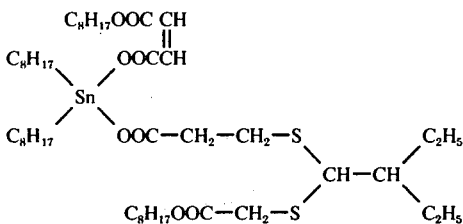

It was prepared by the same method as in Example 23 (using dioctyltin oxide 0.1M, instead of dibutyltin oxide).

The product is a light yellow liquid.

Analysis

| | Found | | Calculated |
|---|---|---|---|
| Sn = | 11.8% | Sn = | 12.3% |
| S = | 6.53% | S = | 6.6% |

Its structure was also confirmed by I.R. and N.M.R. analysis.

EXAMPLE 27

The stabilizers of the present invention can be used with halogen containing vinyl and vinylidene resins in which the halogen is attached directly to the carbon atoms of the polymer chain. Preferably the resin is vinyl halide resin, especially a vinyl chloride resin.

The stabilizers of the present invention can be incorporated with resin by admixing in an appropriate mill or mixer or by any of the other well known methods provided for uniform distribution throughout the resin composition. Thus mixing can be accomplished by milling on rolls at 100°–160° C. In addition to the novel stabilizers these can also be incorporated with resin conventional additives such as plasticizers, pigments, filters, dyes and ultraviolet absorbing agents.

If a plasticizer is employed, it is used in conventional amounts eg. 30 to 150 parts per 100 parts of resin. Typical plasticizers are di-2-ethylhexyl phthalate, dibutyl sebacate and di-iso-phthalate.

The tin containing stabilizers are normally used in an amount of 0.01 to 10% by weight of the resin. More preferably 0.2 to 5% of the tin compound is used by weight of the resin.

A number of compounds of the present invention were tested for initial color development against known stabilizers on an equal tin basis and it was shown that they compacted favorably (see Table I).

The following example illustrates the stabilizing effect of the compounds of the present invention (with and without additives) in comparison with known stabilizers (i.e. Mellite 31C or dibutyltin bis(isooctyl thioglycollate) or dioctyltin bis(isooctyl thioglycollate) containing equal amount of tin rigid P.V.C. composition.

A series of rigid (not plasticized) formulation was prepared having following composition:

a. Corvic D55/09 ... 100 parts
b. Plastilube 30— Marked T if added and the amount present in part per 100 parts of polymer are indicated inside the brackets. In many instances of the present invention plastilube has not been added to the polymer due to the reason that, many of the compounds tested are themselves acting as lubricant during milling at 155° C.
c. Stabilizers and additives—All examples in Table III have been tested (with and without additives) separately in comparison with Mellite 31C or pure dibutyltin bis(isooctyl thioglycollate) or pure dioctyltin bis(isooctyl thioglycollate) containing equal amount of tin in definite amount of corvic D55/09 (usually 300 gms.).

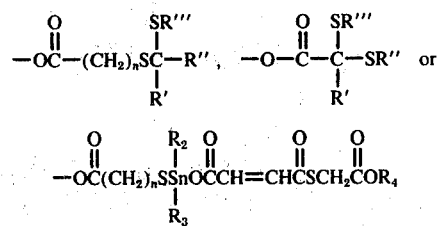

wherein R' is a hydrogen, $C_1$ to $C_{20}$ alkyl, cycloalkyl, aryl group
R'' is a $C_1$ to $C_{20}$ alkyl, aryl or hydroxyphenyl or methoxyphenyl group or $CH_2COOR_5$ where $R_5$ is an alkyl group of 1 to 8 carbon atoms;
R''' is $R_6$ or is $(CH_2)_n COOR_6$ where $R_6$ is an alkyl group of from 1 to 20 carbon atoms, a cycloalkyl or an aryl group, $m$ is an integer from 3 to 7 and $n$ is an integer from 1 to 4;
$R_2$ and $R_3$ are selected from the same group as R;
$R_4$ is selected from the same group as R';

TABLE III

Testing of stabilizers (with and without additives) in comparison with Mellite 31C or dibutyltin bis(iso-octyl thioglycollate) or dioctyltin bis(iso-octyl thioglycollate) containing equal amount of tin in P.V.C.

| S No. | Example No. | Example — with and without additives or pure stabilizers | Parts of compound or mixture of compounds in 100 Parts of P.V.C. | Colour on Gardner scale after given time (in min) at 190° C | | | |
|---|---|---|---|---|---|---|---|
| | | | | 0 | 5 | 10 | 15 |
| (1) | Example 21 | a. M31C + T(0.5) | a. Tin equivalent to b | 0 | 0 | 1–2 | 5 |
| | | b. Exp. 21 + T(0.33) | b. 1.97 Part | 0 | 0 | 1 | 3 |
| | | c. Exp. 21(95) + B(5) + T(0.33) | c. Tin equivalent to b | 0 | 0 | 1 | 1–2 |
| (2) | Example 25 and Example 26 | a. Example 25 | a. 1.66 Part | 0 | 0 | 1–2 | 2–3 |
| | | b. OC$_2$Sn(SCH$_2$COOC$_8$H$_{17}$) + T(0.5) | b. Tin equivalent to a | 0 | 3 | 6–7 | — |
| | | c. Example 26 | c. " | 0 | 0 | 1 | 4 |
| (3) | Example 26 | a. Example 26 | a. 1.33 Part | 0 | 0 | 1–2 | |
| | | b. OC$_2$Sn(SCH$_2$COOC$_8$H$_{17}$)$_2$ + T(0.5) | b. Tin equivalent to a | 2 | 4 | 8 | |
| | | c. Exp. 26 + A (0.2) | c. " | 0 | 0 | 3 | |
| | | d. Exp. 26 + C (0.2) | d. " | 0 | 0 | 3 | |
| | | e. Exp. 26 + F (0.2) | e. " | 0 | 0 | 4 | |
| (4) | Example 23 | a. Bu$_2$Sn(SCH$_2$ COOC$_8$H$_{17}$)$_2$ + T(0.5) | a. 0.9 Part | 0 | 3 | 7 | |
| | | b. Example 23 | b. Tin equivalent to a | 0 | 0 | 2 | |
| (5) | Example 24 | a. Example 24 | a. 1.66 Part | 0 | 0 | * | |
| | | b. Bu$_2$Sn(SCH$_2$COOC$_8$H$_{17}$)$_2$ + T(0.5) | b. Tin equivalent to a | 0 | 1–2 | 6 | |

* represent slightly pink tinge
A represents D.E.S. (Butyl epoxy stearate)
B represents BuSn(SCH$_2$COOC$_8$H$_{17}$)$_3$
D represents Mellite 313
( ) shows the parts of compound and also:-
F represents iso-octyl thioglycollate
T represents Plastilube 30

What is claimed is:
1. Chemical compounds of the general formula

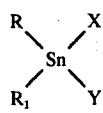

wherein R and $R_1$ are individually selected from the group consisting of alkyl groups containing between 1 and 12 carbon atoms, cycloalkyl and phenyl groups;
X is a group of the formula Y is selected from the same group as X or a member selected from the group consisting of —S(CH$_2$)$_n$COOR$_7$, —OOCCH=CH COOR$_7$ and —OOCCH=CH COSCH$_2$COOR$_7$, with the proviso that Y is

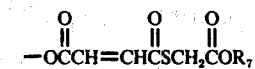

when X is

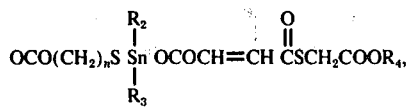

where $R_7$ is an alkyl group of from 1 to 20 carbon atoms, a cycloalkyl or phenyl group or a group of the formula

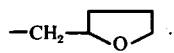

2. A compound according to claim 1 wherein each of R and $R_1$ are the same.

3. A compound according to claim 1 wherein R and $R_1$ are alkyl groups of from 4 to 8 carbon atoms.

4. A compound according to claim 1 wherein $R_6$ is an alkyl group having from 8 to 16 carbon atoms.

5. A compound according to claim 1 wherein $R_7$ is an alkyl group of from 8 to 16 carbon atoms.

6. A compound according to claim 1 wherein R' is hydrogen.

7. A compound according to claim 1 wherein R'' is an alkyl group.

8. A compound according to claim 1 wherein R'' is of the formula

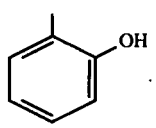

9. A compound according to claim 1 wherein R'' is of the formula

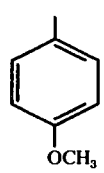

10. A compound according to claim 1 having the formula

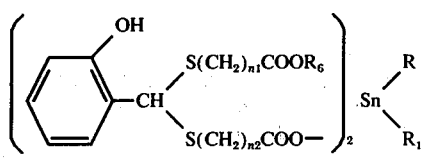

where $n_1$ and $n_2$ may be the same or different and are each either 1 or 2.

11. A compound according to claim 1 having the formula

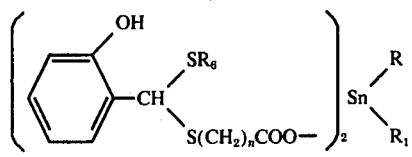

12. A compound according to claim 1 having the formula

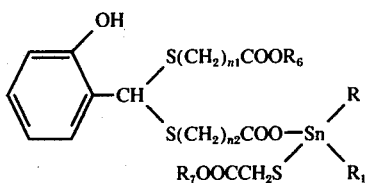

where $n_1$ and $n_2$ are the same or different and are each either 1 or 2.

13. A compound according to claim 1 having the formula

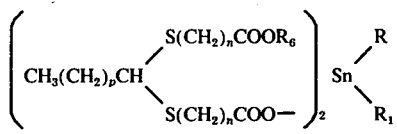

where $p$ is an integer from 1 to 12.

14. A compound according to claim 1 having the formula

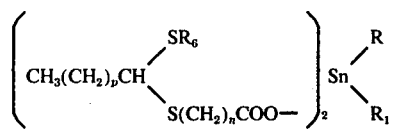

where $p$ is an integer from 1 to 12.

15. A compound according to claim 1 having the formula

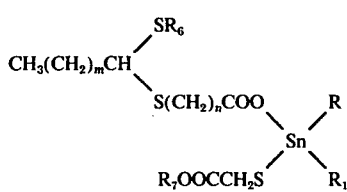

where $m$ is an integer from 1 to 12.

16. A compound according to claim 1 having the formula

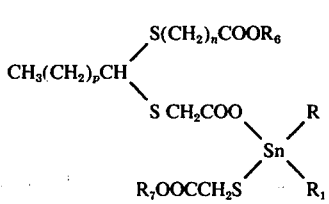

in which $p$ is an integer from 1 to 12.

17. A compound according to claim 1 having the formula

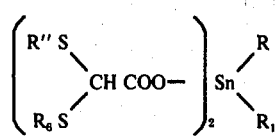

18. A compound according to claim 1 having the formula

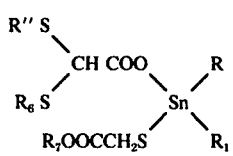

19. A compound according to claim 1 having the formula

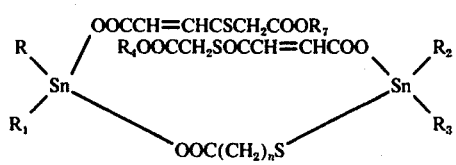

20. A compound according to claim 1 having the formula

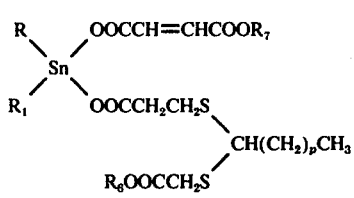

where $p$ is an integer from 1 to 12.

21. A compound according to claim 1 having the formula

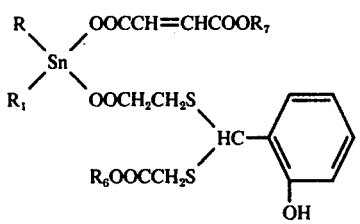

22. A compound according to claim 1 having the formula

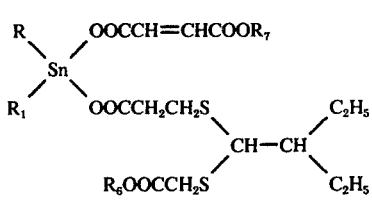

23. A compound according to claim 1 having the formula

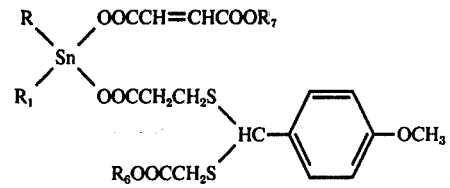

24. A compound according to claim 1 wherein R'' is $C_{1-20}$ alkyl, hydroxyphenyl or methoxy phenyl or the group $CH_2COOR_5$.

25. A compound according to claim 1 wherein X is

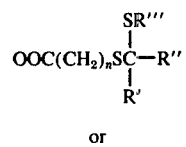

or

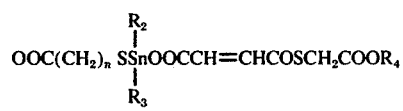

and Y is the same as X or is of formula OOCCH=CHCOOR$_7$ or OOCCH=CHCOSCH$_2$COOR$_7$ with the proviso that Y is OOCCH=CHCOSCH$_2$COOR$_7$ when X is

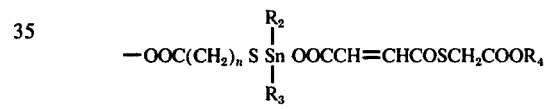

26. A compound according to claim 25 wherein R'' is $C_{1-20}$ alkyl, hydroxyphenyl or methoxyphenyl or the group $CH_2COOR_5$.

27. A compound according to claim 25, wherein R' is hydrogen, $C_{1-20}$ alkyl or cycloalkyl, R''' is R$_6$ or CH$_2$COOR$_6$ where R$_6$ is alkyl or cyclo alkyl and R$_7$ is alkyl, cycloalkyl or

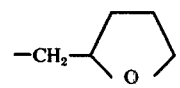

28. A compound according to claim 27 wherein R'' is $C_{1-20}$ alkyl, hydroxyphenyl or methoxyphenyl or the group $CH_2COOR_5$.

29. A compound according to claim 25 wherein X is

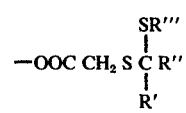

and Y is the same as X or of formula OOCCH=CHCOOR$_7$.

30. A compound according to claim 27 wherein X is

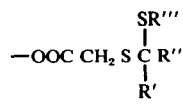

and Y is the same as X or of formula OOCCH=CH-COOR$_7$.

31. A compound according to claim 20 wherein X is

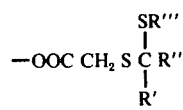

and Y is the same as X or of formula OOCCH=CH-COOR$_7$.

32. A compound according to claim 29 wherein R and R$_1$ are the same, R$_6$ is C$_{8-16}$ alkyl, R$_7$ is C$_{8-16}$ alkyl and R' is hydrogen.

33. A compound according to claim 32 wherein R and R$_1$ are C$_{4-8}$ alkyl.

34. A compound according to claim 25 wherein X is

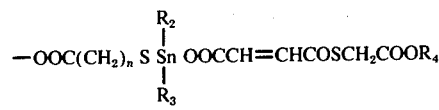

35. A compound according to claim 34 wherein R$_1$, R$_1$, R$_2$ and R$_3$ are the same and are alkyl groups of 4–8 carbon atoms, and R$_4$ and R$_7$ are alkyl groups.

* * * * *

UNITED STATES PATENT AND TRADEMARK OFFICE
CERTIFICATE OF CORRECTION

PATENT NO. : 4,020,090
DATED : April 26, 1977
INVENTOR(S) : JOHN DESMOND COLLINS et al It is certified that error appears in the above-identified patent and that said Letters Patent are hereby corrected as shown below:

Column 3, line 48, delete the formula which appears at the end of the line;

Column 3, line 51, replace " 'SH" with --R'''SH--.

Column 7, line 30, replace "$S_1$" with --$R_1$--. This correction is to the symbol appearing in the lower left-hand portion of the formula and appears to fall on the left end of line 30.

Column 31, line 11, replace "20" with --28--.

Signed and Sealed this

Twenty-fifth Day of April 1978

[SEAL]

Attest:

RUTH C. MASON
Attesting Officer

LUTRELLE F. PARKER
Acting Commissioner of Patents and Trademarks